US007783095B2

(12) United States Patent
Carneiro et al.

(10) Patent No.: US 7,783,095 B2
(45) Date of Patent: Aug. 24, 2010

(54) SYSTEM AND METHOD FOR FETAL BIOMETRIC MEASUREMENTS FROM ULTRASOUND DATA AND FUSION OF SAME FOR ESTIMATION OF FETAL GESTATIONAL AGE

(75) Inventors: Gustavo Carneiro, Princeton, NJ (US); Sara Good, Pleasanton, CA (US); Bogdan Georgescu, Plainsboro, NJ (US); Paolo Favaro, Edinburgh (GB); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 932 days.

(21) Appl. No.: 11/463,341

(22) Filed: Aug. 9, 2006

(65) Prior Publication Data

US 2007/0081705 A1    Apr. 12, 2007

Related U.S. Application Data

(60) Provisional application No. 60/707,280, filed on Aug. 11, 2005, provisional application No. 60/707,281, filed on Aug. 11, 2005, provisional application No. 60/707,634, filed on Aug. 12, 2005.

(51) Int. Cl.
*G06K 9/00* (2006.01)
(52) U.S. Cl. .................................... 382/128
(58) Field of Classification Search ............. 382/128
See application file for complete search history.

(56) References Cited

U.S. PATENT DOCUMENTS 5,546,807 A * 8/1996 Oxaal et al. ............... 73/606

6,996,549 B2 * 2/2006 Zhang et al. ............... 706/16
7,110,583 B2 * 9/2006 Yamauchi .................. 382/128
2005/0277912 A1 * 12/2005 John ......................... 604/890.1

OTHER PUBLICATIONS

Chen et al., Head tracking with shape modeling and detection, May 9-11, 2005, Proceedings: The 2nd Canadian Conference on Computer and Robot Vision, 2005, pp. 483-488.*
Prakash et al., Fetal Lung Maturity Analysis Using Ultrasound Image Features, Mar. 2002, IEEE Transactions on Information Technology in Biomedicine, vol. 6, No. 1, pp. 38-45.*
Nelson et al., Visulization of 3D Ultrasound Data, Nov. 1993, IEEE Computer Graphics & Applications, pp. 50-57.*
Mowforth et al., Model Based Tissue Differentiation in MR Brain Images, Sep. 25-28, 1989, Proceedings of the Fifth Alvey Vision Conference, pp. 67-71.*
Comaniciu, Dorin "Nonparametric Information Fusion for Motion Estimation".

* cited by examiner

*Primary Examiner*—Matthew C Bella
*Assistant Examiner*—Dennis Rosario

(57) ABSTRACT

A method for segmenting and measuring anatomical structures in fetal ultrasound images includes the steps of providing a digitized ultrasound image of a fetus comprising a plurality of intensities corresponding to a domain of points on a 3-dimensional grid, providing a plurality of classifiers trained to detect anatomical structures in said image of said fetus, and segmenting and measuring an anatomical structure using said image classifiers by applying said elliptical contour classifiers to said fetal ultrasound image, wherein a plurality of 2-dimensional contours characterizing said anatomical structure are detected. The anatomical structure measurement can be combined with measurement of another anatomical structure to estimate gestational age of the fetus.

18 Claims, 9 Drawing Sheets

SYSTEM AND METHOD FOR FETAL BIOMETRIC MEASUREMENTS FROM ULTRASOUND DATA AND FUSION OF SAME FOR ESTIMATION OF FETAL GESTATIONAL AGE

CROSS REFERENCE TO RELATED UNITED STATES APPLICATIONS

This application claims priority from "A method and system for automatic fetal biometric measurements from 3D ultrasound data", U.S. Provisional Application No. 60/707,280 of Favaro, et al., filed Aug. 11, 2005, "Real-Time One-Click Solutions for 2D Ultrasound Fetal Measurements", U.S. Provisional Application No. 60/707,281 of Favaro, et al., filed Aug. 11, 2005, and "A Method for Joint Estimation of Fetal Gestational Age Based on Robust Fusion of Ultrasound Biometric Measurements", U.S. Provisional Application No. 60/707,634 of Favaro, et al., filed Aug. 12, 2005, the contents of all of which are incorporated herein by reference.

TECHNICAL FILED

This invention is directed to the acquisition and analysis of biometric data in ultrasound images.

DISCUSSION OF THE RELATED ART

Accurate fetal ultrasound (US) measurements are one of the most important factors for high quality obstetrics health care. The most common fetal ultrasound measurements are fetal crown-rump length (CRL), head circumference (HC), abdominal circumference (AC), bi-parietal diameter (BDP), occipital-frontal diameter (OFD) and femur length (FL). These measurements are used to estimate the gestational age (GA) of the fetus.

There has been little work in the automatic segmentation of fetal ultrasound (US) images, while an increasing number of more accurate GA charts have become available. This indicates that automatic obstetric measurements based on US images is an unsolved issue.

The current art of HC, BPD, FL and AC measurements are based either on 2D ultrasound imaging or 3D volume imaging. In both cases the search for the standardized plane is cumbersome process. The manual search for the standardized plane in 2D ultrasound images is one of the main contributors to the excessive length to clinical obstetric examinations. While 3D imaging has the potential to shorten the exam time and to make the measurements less operator-dependent the need to search for the standardized plane is not removed.

As a rule, several biometric measurements are performed simultaneously. For example, BDP, OFD, and HC are measured in the same plane. Also, the current clinical workflow of obstetrics health care requires that an ultrasound exam include the head, abdomen and femur measurements. The measurements are often repeated.

HC and BPD measurements require the fitting of the head diameter and an ellipse that approximates the shape of the head displayed in the input image slice. Currently, biometrics are performed either completely manually or semi-automatically wherein the operator has to mark several control points that need to: (1) outline the position, shape and orientation of ellipse for AC and HC measurements; (2) mark the beginning and end of the line that corresponds to BDP, OFD and FL. Measurements are always performed in a standard plane. In the case of the AC and HC measurements, the actual shapes of the abdomen and head, respectively might not be perfectly approximated with ellipses. This is an additional source of errors and uncertainties and contributes to the unwanted operator-dependencies.

2D ultrasound obstetrics measurements require a tedious search for the optimal plane in the adverse conditions of constant fetal motion. A search for the plane is performed on-line in real-time by an operator who manipulates the ultrasound probe and monitors the ultrasound system until the optimal plane is found. At that moment the operator needs to instantaneously freeze the ultrasound snapshot and outline the contour of the structure of interest (e.g. head, abdomen or femur) using the calipers provided. Studies indicate that 2D ultrasound obstetrics exams that include typical biometrical fetal measurements take on average between 30 and 60 minutes depending on the clinical state of the fetus.

Automatic standardized plane searches in 3D ultrasound volumes can potentially be significantly easier than in 2D ultrasound images as it can be performed off-line using the visualization tools of the workstation rather than the ultrasound transducer directly on the subject. Some recent studies indicate that for obstetrics health care there is a potential 300% improvement in the scanning, reconstruction and measuring time of 3D ultrasound systems over 2D imaging. However, search for the standardized plane in 3D volumes is still time consuming as it requires the operator to learn to use appropriate visualization tools and sequentially apply translation and rotations of the visualized plane until the standardized plane is found.

The main drawback of the current methods for the fetal biometrics measurements is the need to search for the standardized plane. This drawback occurs in both 2D and 3D ultrasound fetal imaging. For example, the standardized plane for the head circumference (HC) and bi-parietal diameter (BPD) measurements must include cavum septum pellucidum, thalami and falx celebri, and the falx of the brain must divide the head symmetrically into two lobes. Similarly, accurate measurement of the abdominal circumference (AC) requires the image to contain the stomach and the middle third of the umbilical vein and spine.

The most common interpreted measurement is fetal gestational age (GA), which refers to the length of pregnancy after the first day of the last menstrual period (LMP) and is usually expressed in weeks and days. Accurate estimation of gestation age (GA) is of extreme importance for estimating the date of confinement, estimating the expected delivery date, assessing of fetal size and monitoring of fetal growth. Gestational age is not only important for the expecting mother, but also for health providers, so they may plan various screening tests and assessments.

Extensive research in the last 30 years has yielded numerous population-specific charts of fetal biometry vs. gestational age, usually for the 11-41 week period of gestation. Current charts in use were created applying some exclusion principles (outlier removal), and statistical analyses were performed typically using the polynomial regression models. Most current charts include regression equations, means and $95^{th}$ reference intervals for standard biometric measurements. The extensive clinical validation has led to adoption of some charts by national ultrasound and obstetrics committees and standardization bodies.

Current estimators of GA based on fetal biometric parameters are subject to numerous inaccuracies that result in large bias and variance. While the menstrual history and clinical examination can be used to estimate the GA, both are subject to considerable error. As a widely accepted current art, 2D, 3D and 4D ultrasound imaging provides the direct means to measure fetal biometrics. However, due to a number of factors, such as operator-dependency and poor quality of images, estimation of GA is subject to errors.

In addition, GA estimates can differ within the same fetus due to different measurements. Individual errors in the measurements can result from artifacts in the ultrasound images or are operator-dependent. Even for a highly trained operator, there are visible discrepancies in GA estimations coining from different sources.

Despite the ongoing research, the charts currently in use are also subject to inaccuracies either due to the lack of the data for the second trimester charts or due to the individual size variations in the third trimester. Generally, the later the gestational age, the higher the uncertainty in GA estimation. Towards the end of the pregnancy, the GA estimations have average confidence intervals of plus/minus three weeks due to the weight gain of the fetus. This indicates serious difficulties in estimation of GA from a large population of normal pregnancies when examination is performed to a standard protocol by experienced operators.

There have been attempts to combine the GA estimation from multiple modalities, for example by combining the ultrasound measurements with the dale of last menstrual cycle. Detailed analysis from large databases has not shown any advantage in using these rules. Current systems do not explicitly take into account measurements as they are bundled into the confidence intervals of GA estimations. Often there are no means to compute the uncertainty of measurements, and often those uncertainties are simply discarded.

SUMMARY OF THE INVENTION

Exemplary embodiments of the invention as described herein generally include methods and systems for automatically detecting, segmenting, and measuring fetal anatomical structures from ultrasound images in real-time, and for the fusion of multiple fetal biometric ultrasound (US) measurements for robust gestation age (GA) estimation. The following obstetric measurements are considered: head circumference (HC), biparietal diameter (BPD), abdominal circumference (AC), and femur length (FL). The measurements can be performed in 2D images obtained from a 2D/3D US probe or a 3D US volume. A system according to an embodiment of the invention automatically reconstructs the 3D shape of the top portion of the head and measures the biparietal diameter and head circumference. The uncertainties and errors in the measurements are modeled with a noise distribution. Each individual noisy measurement is mapped to the to corresponding biometric chart to estimate the distribution of the gestational age using Monte Carlo sampling. Multiple GA estimates are fused using the variable bandwidth density-based fusion (VBDF) to obtain a single GA estimation.

A method and system according to an embodiment of the invention for measurement of fetal biometrics parameters directly in 3D US volumes can minimize the amount of operator involvement. The system can automatically find the plane to measure the HC, OFD, BPD, AC, and FL. Thus, the need for the manual standardized plane search is removed.

A method according to an embodiment of the invention leverages the fact that multiple measurements that can yield multiple GA estimations are readily available, and merges estimations from multiple biometric measurements in order to reduce the bias and variance of GA estimation. A method according to an embodiment of the invention provides completely automatic detection and measurement of the head, abdomen, and femur parameters using the respective detectors trained on the large datasets of annotated studies.

Embodiments of the invention can improve the clinical workflow by simplifying the acquisition of fetal measurements using 2D and 3D ultrasound systems, minimizing the operator-dependency of the measurements, reducing the exam time, increasing patient throughput and limiting the repetitive stress injuries (RSI) of sonographers. Methods according to embodiments of the invention are not limited to common measurements, such as HC, AC, BDP, OFD, and FL, but can be directly applied to any additional measurement provided the corresponding GA chart. The ultrasound modality is not important in the sense that an information fusion according to an embodiment of the invention can be applied to 2D, 3D or 4D (3D+time) measurements as long as the measurements are paired with their uncertainties.

According to an aspect of the invention, there is provided a method for segmenting and measuring anatomical structures in fetal ultrasound images, the method including providing a digitized ultrasound image of a fetus comprising a plurality of intensities corresponding to a domain of points on a 3-dimensional grid, providing a plurality of classifiers trained to detect anatomical structures in said image of said fetus, and segmenting and measuring an anatomical structure using said image classifiers by applying said elliptical contour classifiers to said fetal ultrasound image, wherein a plurality of 2-dimensional contours characterizing said anatomical structure are detected.

According to a further aspect of the invention, the classifiers are trained to detect anatomical structures by providing a set of ellipses to represent contours of said anatomical structures, providing a database of pairs of contours and intensity sets that are represented by said contour, using a boosting technique with said database for training said classifiers to correctly detect contour/intensity-set pairs, but reject most non-contour/intensity-set pairs, and incorporating some non-contour/intensity-set pairs into said classifier, wherein said trained classifier outputs an image model that maps a set of image intensities to a likelihood of a presence of an anatomical structure.

According to a further aspect of the invention, the classifiers explicitly incorporate translation, rotation, and scaling of said intensity-sets.

According to a further aspect of the invention, the contour/intensity pairs in said database were selected by one or more experts in obstetrics.

According to a further aspect of the invention, segmenting and measuring comprise sweeping said 3-dimensional ultrasound fetal image wherein a plurality of planes are obtained by uniformly sampling the azimuthal and elevation angles, and for each plane of said plurality of planes, applying said contour classifiers to a plurality of locations, scales, orientations, and aspect ratios.

According to a further aspect of the invention, the method comprises propagating said 2-dimensional contours to form a 3-dimensional shape of said anatomical structure.

According to a further aspect of the invention, training said contour classifier comprises registering said contours to ellipses by learning global transformations, wherein global transformations include translation, scale, rotation, and aspect ratio, and applying an inverse global transformation.

According to a further aspect of the invention, the ellipses include contours that deviate slightly from a perfect ellipse.

According to a further aspect of the invention, the method comprises combining said anatomical structure measurement with measurement of another anatomical structure to estimate gestational age of said fetus.

According to a further aspect of the invention, combining said anatomical structure measurement with another anatomical structure measurement comprises approximating a distribution and uncertainty for each measurement, projecting each measurement distribution and uncertainty onto a gestational age axis of a gestational biometric chart to obtain a gestational age hypothesis for each measurement, estimating the distribution of the gestational age hypotheses, and fusing said age hypotheses using a variable bandwidth density-based fusion wherein a majority vote of said multiple hypotheses estimates said gestational age.

According to a further aspect of the invention, the anatomical measurements include two or more measurements selected from the group including of fetal crown-rump length, head circumference, biparietal diameter, abdominal diameter, occipital frontal diameter, and femur length.

According to another aspect of the invention there is provided a program storage device readable by a computer, tangibly embodying a program of instructions executable by the computer to perform the method steps for segmenting and measuring anatomical structures in digital fetal ultrasound images.

DETAILED DESCRIPTION OF THE PREFERRED EMBODIMENTS

Figure 1:
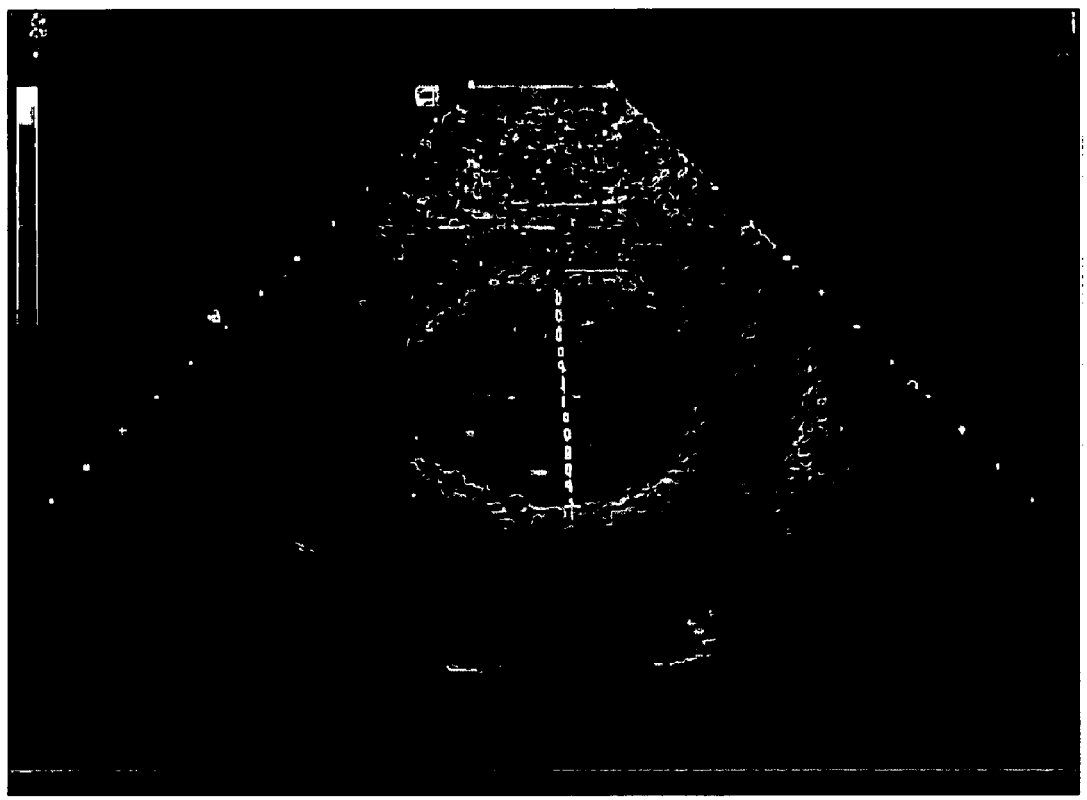
FIG. 1 depicts a screen shot from a computer system monitor that illustrates head contour detection and the corresponding HC measurement, according to an embodiment of the invention.

Exemplary embodiments of the invention as described herein generally include systems and methods for automatically detecting, segmenting, and measuring fetal anatomical structures from ultrasound images in real-time, and for the fusion of multiple noisy fetal biometric ultrasound (US) measurements for robust gestation age (GA) estimation. Accordingly, while the invention is susceptible to various modifications and alternative forms, specific embodiments thereof are shown by way of example in the drawings and will herein be described in detail It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Figure 5:
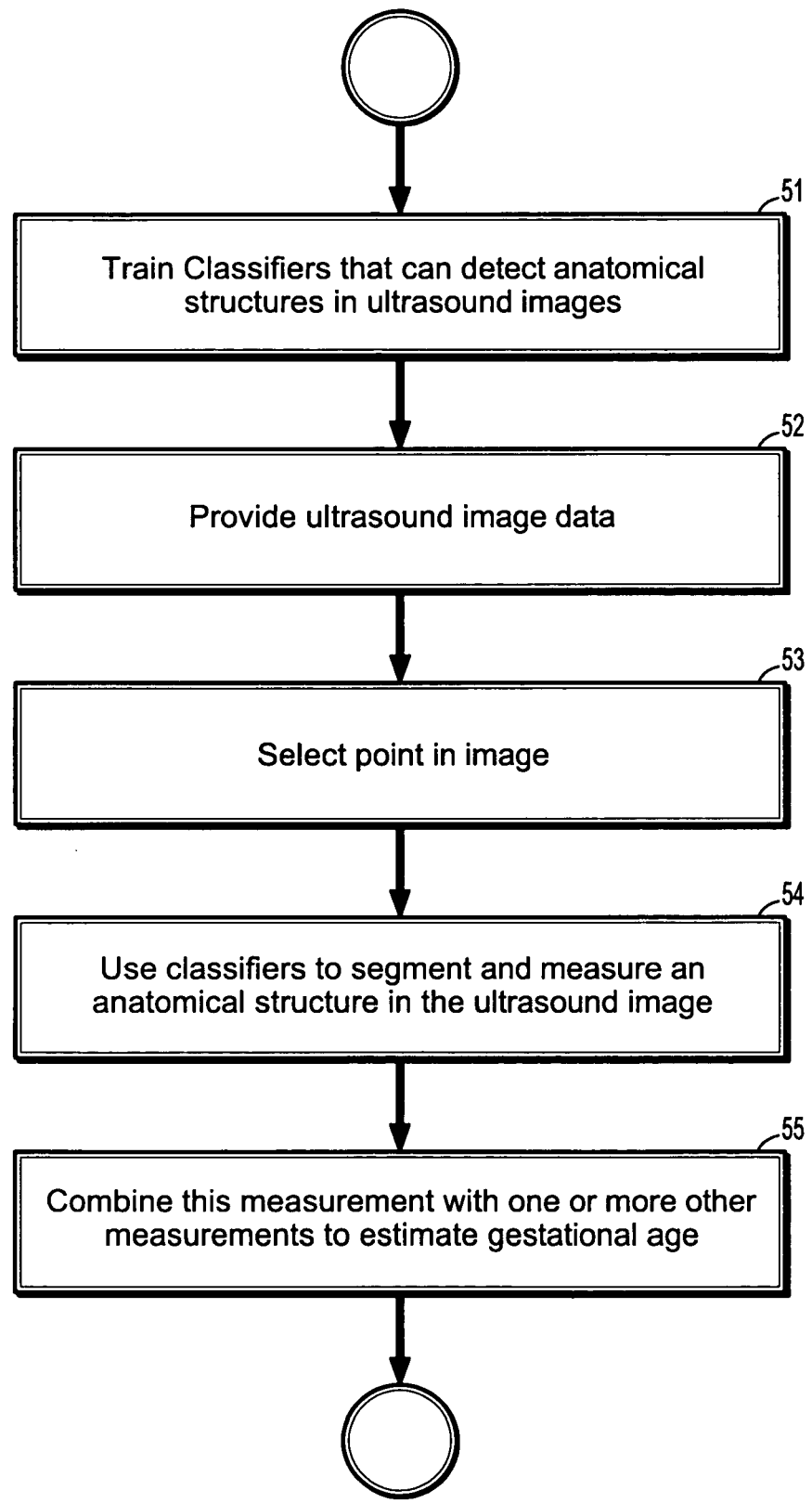
FIG. 5 is a flow chart of a method for automatically detecting, segmenting, and measuring fetal anatomical structures from ultrasound images in real-time, and for fusing these measurements for gestation age estimation, according to an embodiment of the invention.

A flow chart of a method according to an embodiment of the invention for automatically detecting, segmenting, and measuring fetal anatomical structures from ultrasound images in real-time, and for fusing these measurements for gestational age estimation is presented in FIG. 5. Referring to the image, classifiers that can detect anatomical structures, such as the head, abdomen, or femur, are trained at step 51. These classifiers are trained by boosting techniques described below. An ultrasound image, either a 2D slice, a 3D image volume, or a 4D image that includes a time sequence of 3D images, is provided at step 52. A point in the image is selected at step 53. This point selection is performed automatically, possibility off-line. At step 54, the classifiers are used to segment the structure about the selected point, and to obtain measurements of the segmented structure. The measurements of the segmented structure can be combined with one or more other measurements at step 55 to obtain an estimate of the fetal gestational age. Measurements can be fused using variable bandwidth density-based fusion technique, as explained below.

According to an embodiment of the invention, a method to detect and segment anatomical structures in ultrasound data includes automatically segmenting the head, the abdomen and the femur of a fetus to obtain the head circumference (HC), bi-parietal diameter (BPD), abdominal circumference (AC), and femur length (FL), which are indicators of the gestational age (GA). The accuracy of the GA estimate strongly depends on how close the collected data follow the standard protocols for obstetrics measurements. For example, the standard protocol for the BPD measurement states that the user must measure the outer part of the upper side to the inner part of the lower side of the skull. On the one hand, manual segmentation is the most flexible method to obtain obstetric measurements according to the standard protocols, but it requires expert knowledge and it is a time-consuming and error-prone task. On the other hand, automatic localization of the contour is in general less flexible, since such standard protocols are hard to encode in a computationally efficient algorithm, but has the benefit of increasing the reliability and reproducibility of the obstetric measurements. A method according to an embodiment of the invention combines the benefits of both of the above approaches and is automatic.

Such a system can "learn" off-line how to segment objects from examples of segmentations provided by experts (training set), and then use this knowledge to detect on-line the contour on new ultrasound data. A method according to an embodiment of the invention can decrease exam time, reduce the variability of obstetric measurements, and adapts to new standard protocols for segmentation and to different photometric properties of the sonograph in use by simply providing the system with a new training set manually prepared by experts.

According to an embodiment of the invention, a system for real-time ultrasound (US) fetal measurements comprises a 2D ultrasound system equipped with a fetal measurements (FM) button and software that analyzes 2D ultrasound images, automatically extracts fetal measurements (BPD, HC, OFD, AC and FL) and then visualizes the extracted measurement. Under normal usage of the system, the sonographer searches for the anatomical structure of interest, i.e., the head, abdomen or femur of the fetus, by changing position and orientation of the 2D probe and by visually inspecting the real-time imaging of the ultrasound data on the screen. When the correct 2D data has been captured, the sonographer performs the measurement, which triggers the software to analyze the captured data. The software according to an embodiment of the invention automatically detects the head, the abdomen or the femur and then returns the corresponding measurements by visualizing it on the screen superimposed to the 2D data.

FIG. 1 depicts a screen shot from a computer system monitor that illustrates head contour detection and the corresponding HC measurement. The sonographer searches for the head of the fetus and obtains contour and measurements with one click of the mouse. The results are shown in the lower center portion of the screen.

Once a user has provided an ultrasound image showing a standard plane containing one of the following structures, head, abdomen, or femur, it is desired to detect and segment one of these structures in the image.

A detection software system according to an embodiment of the invention includes two parts: training and detection. The training part collects data that has been manually annotated by experts and builds classifiers that can automatically replicate experts' annotation. Classifiers are simple tests based on comparing filter responses to a certain threshold that is computed from the manually annotated data. An exemplary, non-limiting filter uses Haar wavelets.

Figure 6:
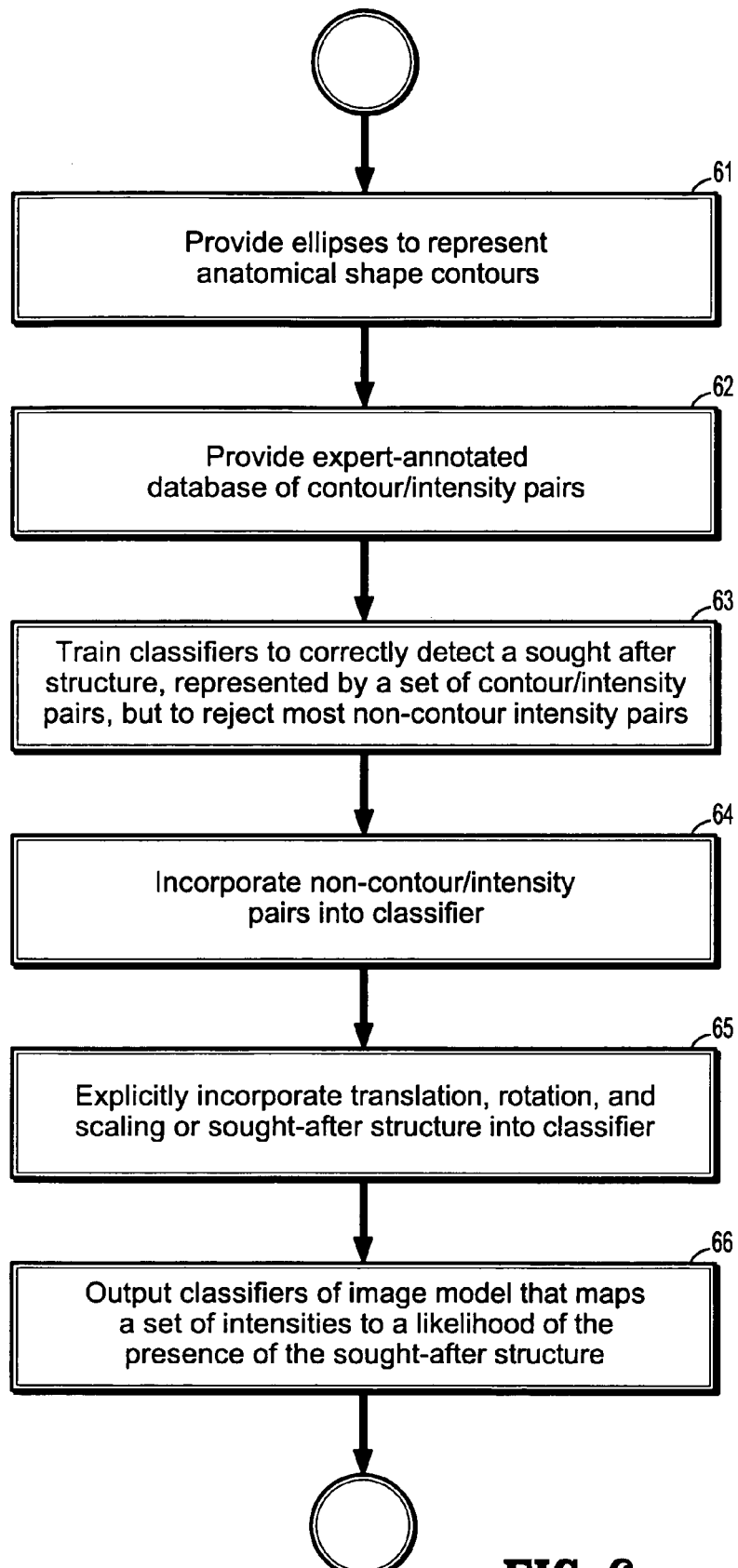
FIG. 6 is a flow chart of a method for training classifiers for segmenting an ultrasound image, according to an embodiment of the invention.

A flow chart of a method according to an embodiment of the invention for training classifiers for segmenting an ultrasound image is shown in FIG. 6. Referring now to the figure, at step 61, before proceeding to detection and segmentation, it is useful to choose a representation of the contour of the anatomical structure of interest and the corresponding image model. The contour of an anatomical structure can be represented by an ellipse. Ellipses allow for a simple (an ellipse is represented with five parameters: major axis, minor axis, 2D center, and orientation), but effective representation as it approximates well the shape of the anatomical structures of interest. Moreover, ellipses are easy to manipulate and fit well with the current method of manual segmentation of fetal anatomies in 2D ultrasound.

A similar simple choice is not possible for the image model. The image model is a function that maps the image intensities to the likelihood of the presence of a given anatomical structure. Due to a number of perturbations introduced by the ultrasound imaging modality, such as the display of nonstructural echoes, removal of real structural echoes and speckle noise, the modeling of such a map is complex. As a result, approximating this mapping via parametric models presents issues because these models do not generalize sufficiently to include all subtleties of the image intensities of the anatomical structure of interest. Therefore, according to an embodiment of the invention, this mapping can be approximated with a non-parametric discriminative model, where the image model is represented by a collection of samples of pairs (contour, intensity). According to an embodiment of the invention, two classes of objects are of interest: the pairs (contour, intensity) and (non-contour, intensity).

A database of expert annotations is provided at step 62. This database is exploited to detect and segment the same type of anatomical structures in previously unseen ultrasound images. Database-guided segmentation refers to the process of implicitly encoding the prior knowledge embedded in expert annotated databases. This requires a large database containing the contour annotation of the anatomical structures of interest provided by experts.

A non-parametric discriminative model according to an embodiment of the invention can be built using a large collection of samples of pairs (contour/non-contour, intensity) annotated by experts. The compilation of a database of annotated samples comprises a first stage of a training process. The next stage of training comprises the estimation of the mapping function, from image intensities to the likelihood of the presence of an anatomy of interest, as described above, by constructing a number of detectors. The desired behavior of a detector is to give a positive response when stimulated with a (contour, intensity) pair, and a negative response when stimulated with a (non-contour, intensity) pair. These detectors are built such that they are guaranteed to have this behavior on most of the collected samples, and can be used to directly localize contours in previously unseen images. Boosting techniques to train these detectors are well known in the art, and an exemplary, non-limiting list includes Adaboost, LogitBoost, and the Probabilistic Boosting Tree.

In order to improve the robustness of the detector, a discriminative model according to an embodiment of the invention is built in stages using an approach called bootstrapping. At step 63, a first stage is designed to be very robust in the sense that it does not fail to correctly detect the sought anatomical structure (i.e., the contour/intensity pairs), but at the same it rejects the vast majority of the (non-contour/intensity) pairs. At step 64, the following stages become more tuned to the correct anatomical structure. This is realized by allowing (non-contour/intensity) pairs similar to the anatomy of interest in the database used to estimate the discriminative model. Bootstrapping can reduce detection time by quickly eliminating large areas of the ultrasound image that do not contain the sought anatomy, and improve the accuracy of the detection in the later stages of the model. Testing amounts to applying the computed feature detectors to new data to localize the contour of the object of interest in an automatic fashion. More specifically, the first stage of the non parametric discriminant model is applied to a few samples extracted from the image, and the later stages of the discriminant model is applied only to those samples that survived the first stage, a technique generally known as coarse to fine search.

In order to maintain the same level of accuracy, the number of samples that are required in the non-parametric representation of the image formation model according to an embodiment of the invention increases as the complexity (variability) of the map increases, in particular, as the dimensionality of its domain is increased. Hence, at step 65, the complexity of the map is limited in an embodiment of the invention by explicitly modeling some global transformations of the domain, such as translation, rotation, and scaling of the samples. At step 66, a set of classifiers that can represent the image model are output.

Figure 4:
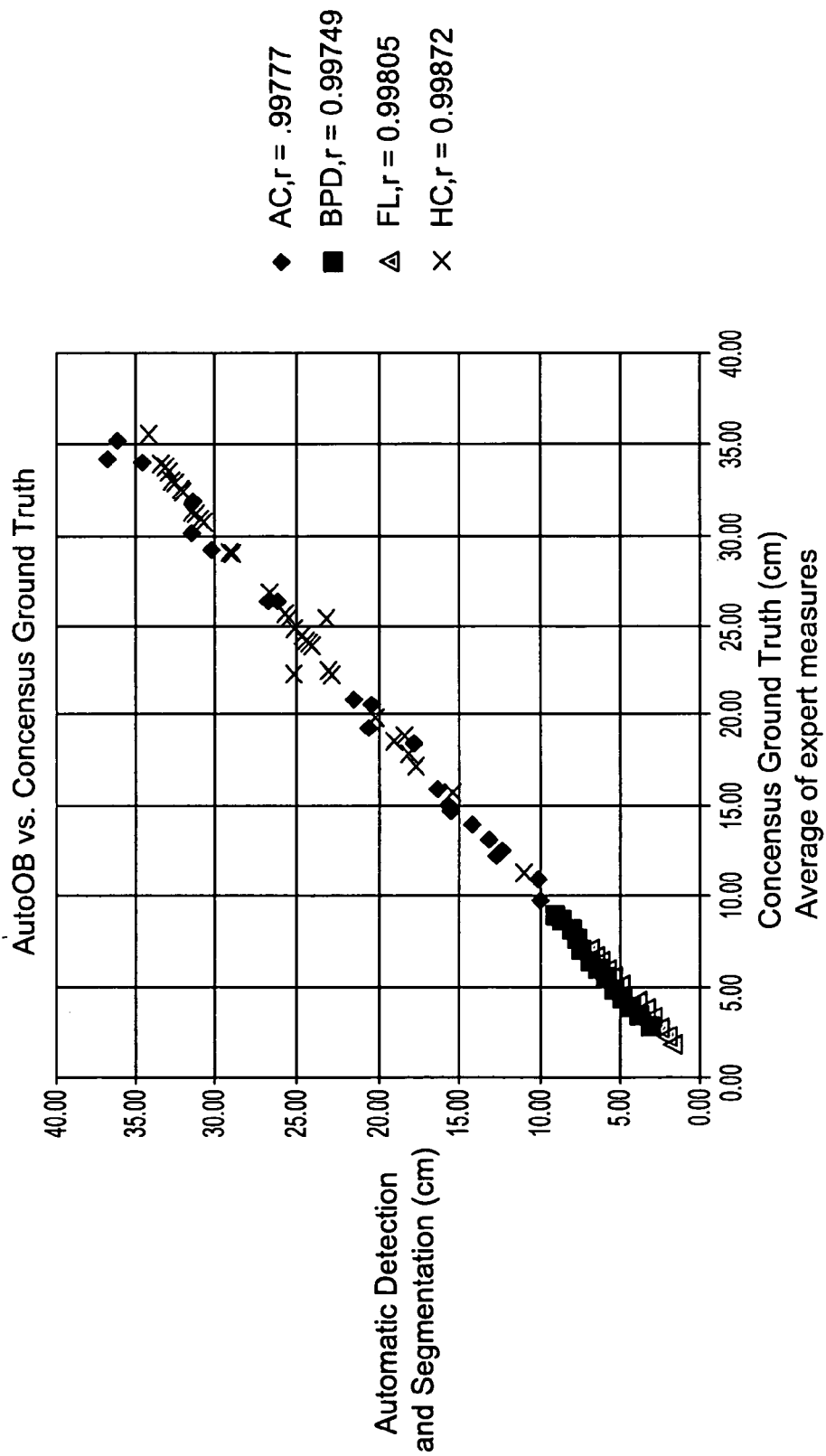
FIG. 4 depicts a scatter plot between the measurement of several anatomical structures provided by an automatic segmentation according to an embodiment of the invention, and the average of three expert annotations of the respective measurements.

FIG. 4 depicts a scatter plot between the measurement of several anatomical structures provided by an automatic segmentation according to an embodiment of the invention, and the average of three expert annotations (i.e., the consensus ground truth) of the respective measurements. The legend on the right shows the labels for each anatomical structure and the respective correlation coefficient. Note that the correlation coefficient $r \in [0,1]$, where 1 means high correlation, measures how correlated the automatic and manual measurements are. This coefficient is defined as the covariance of the two variables (i.e., automatic and manual segmentation measures) over the product of their standard deviations. These results show that method according to an embodiment of the invention works within the error bounds accepted by an expert, which is roughly within 2% to 3% of the correct annotation.

Once classifiers are computed, they can be used in the detection part. Detection involves searching the 2D data provided by the sonographer at run-time for the highest response of the classifiers along all possible translations, rotations and scales.

Figure 2:
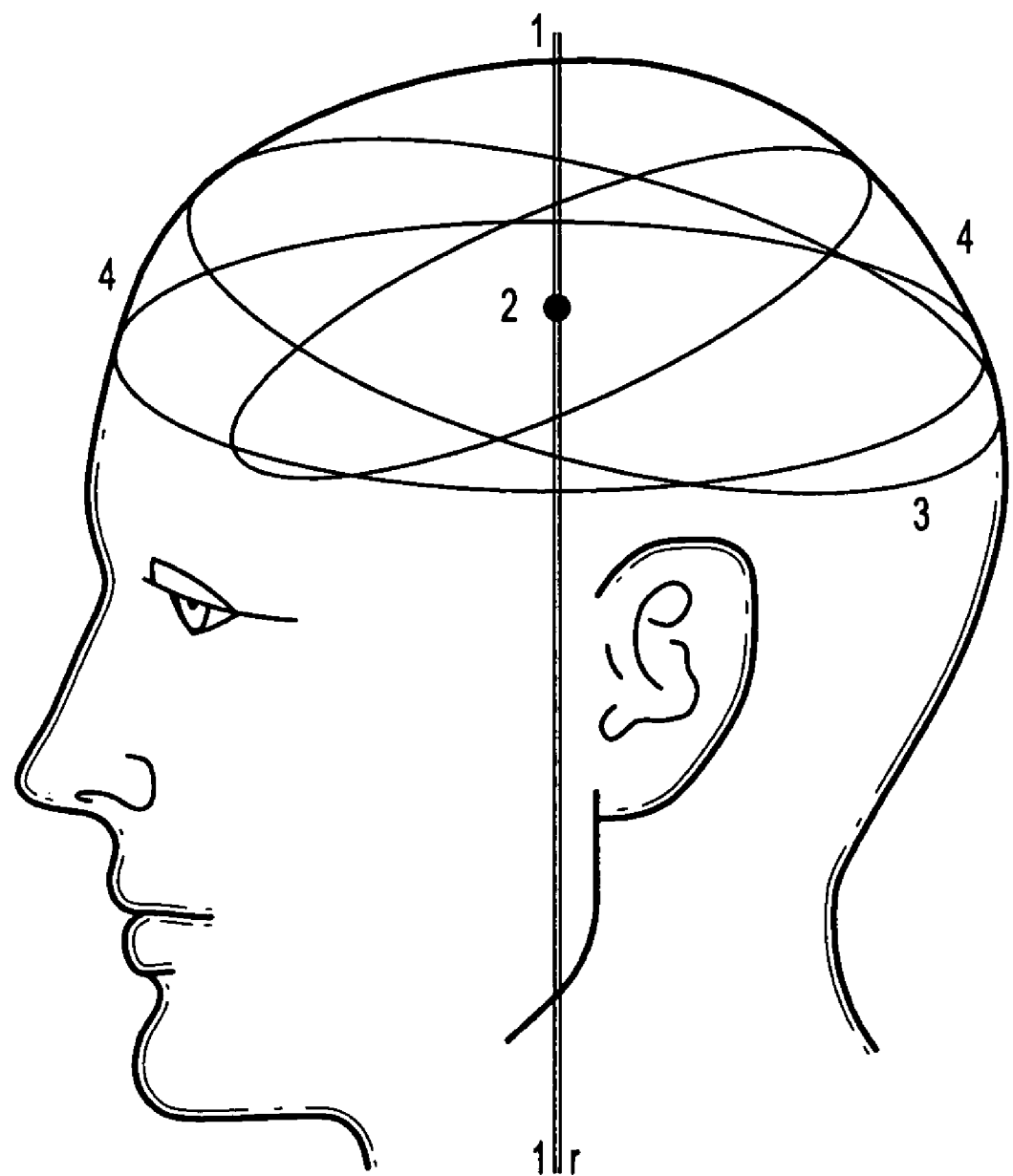
FIG. 2 illustrates a medial line of the fetal head, along with ellipses to estimate the shape, according to an embodiment of the invention.
Figure 7:
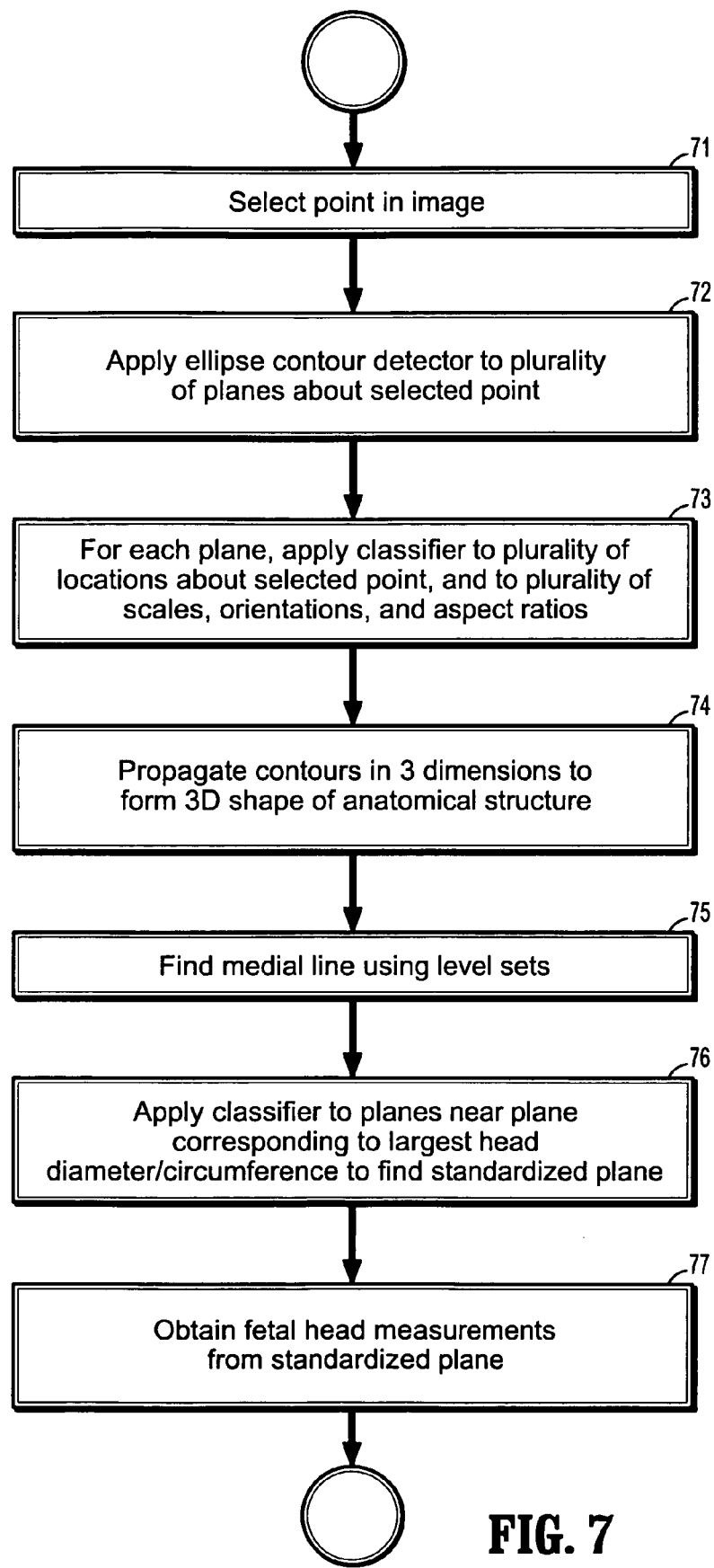
FIG. 7 is a flowchart of a method for automatic fetal head measurements from ultrasound data for the head shown in FIG. 2, according to an embodiment of the invention.

Accordingly to an embodiment of the invention, a flowchart of a method for automatic fetal head measurements from US data is shown in FIG. 7, for a fetal head illustrated in FIG. 2. The system displays a fetal head along with the media line (centerline), shown as the double vertical line (1) in the figure. Referring to FIG. 7, at step 71, the system automatically detects the center point (FIG. 2, ref. 2) in the upper half of the median line. Then, at step 72, a 2D) ellipse contour detection is applied to a plurality of planes containing the center point. A plurality of planes (FIG. 2, ref. 3) that pass through the chosen center point (FIG. 2, ref. 2) are obtained by uniformly sampling the azimuthal and elevation angles in 3D space. An ellipse detector is applied at each plane. The notion of an ellipse can be generalized to include contours that slightly deviate from perfect ellipses. The ellipse detector is based on filter responses and is trained on the large number of annotated studies of 2D fetal head slices. An exemplary, non-limiting filter is based on wavelets. Each ellipse classifier is a non-linear combination (boosting) of a large number (5-200) of simple to compute and fast classifiers. Each annotated study (positive example) includes a shape annotation, such as a parameterized head contour-ellipse, and the appearance map or image. As fetal head contours vary considerably in size and aspect ratio, ranging from perfect circles to high-eccentricity ellipses, the contours are first registered, i.e. normalized, to ellipses by learning the global transformations, such as translation, scale, rotation, and aspect ratio, for each example, and applying the inverse global transformation. At step 73, in each analyzed head slice, the ellipse detector is applied at number of locations, at multiple scales, orientations and aspect ratios. The process of searching for the contour is linear in the number of locations, scales, rotations and aspect ratios searched.

As only one point at the centerline is detected, the search across different locations is confined to a small neighborhood around the given point, due to the high symmetry of the fetal heads and the fact that the center of the ellipse is roughly at the centerline. Thus, the detector need only search across different orientations (angles), scales and aspect ratios. This reduces the computational cost of an exhaustive search. The detector is trained, as described above, to discriminate the ellipse defined as an ellipsoidal region of in the ultrasound image, by designing the detector as a nonlinear combination of a number of simple wavelet features that are distributed along the ellipse. The positive examples are used to learn a joint distribution of images and contours, which can infer the best elliptical shape for the given detected appearance.

At step 74, a shape refinement procedure is applied to infer the best contour associated with the detected appearance. All detected elliptical contours are robustly propagated in 3D to obtain the 3D shape of the upper portion of the head (4) in the form of the mesh or some other representation. The medial line of the head is robustly found at step 75 using classifiers. The standardized plane for the head is very close to the horizontal plane corresponding to the largest circumference (or equivalently, the largest diameter) of the head. Therefore, at step 76, an additional classifier is applied to the several horizontal slices in the vicinity of the plane corresponding to the largest diameter and circumference to identify the standardized plane, The HC and BPD can be measured directly in the detected standardized plane at step 77. The dimensions of the 3D volumes are readily available. Hence, HC and BPD measurements can be trivially converted from pixels (voxels) to millimeters. This allows for automatic gestation age (GA) estimation by simple lookup at the fetal biometrics parameters charts.

Figure 8:
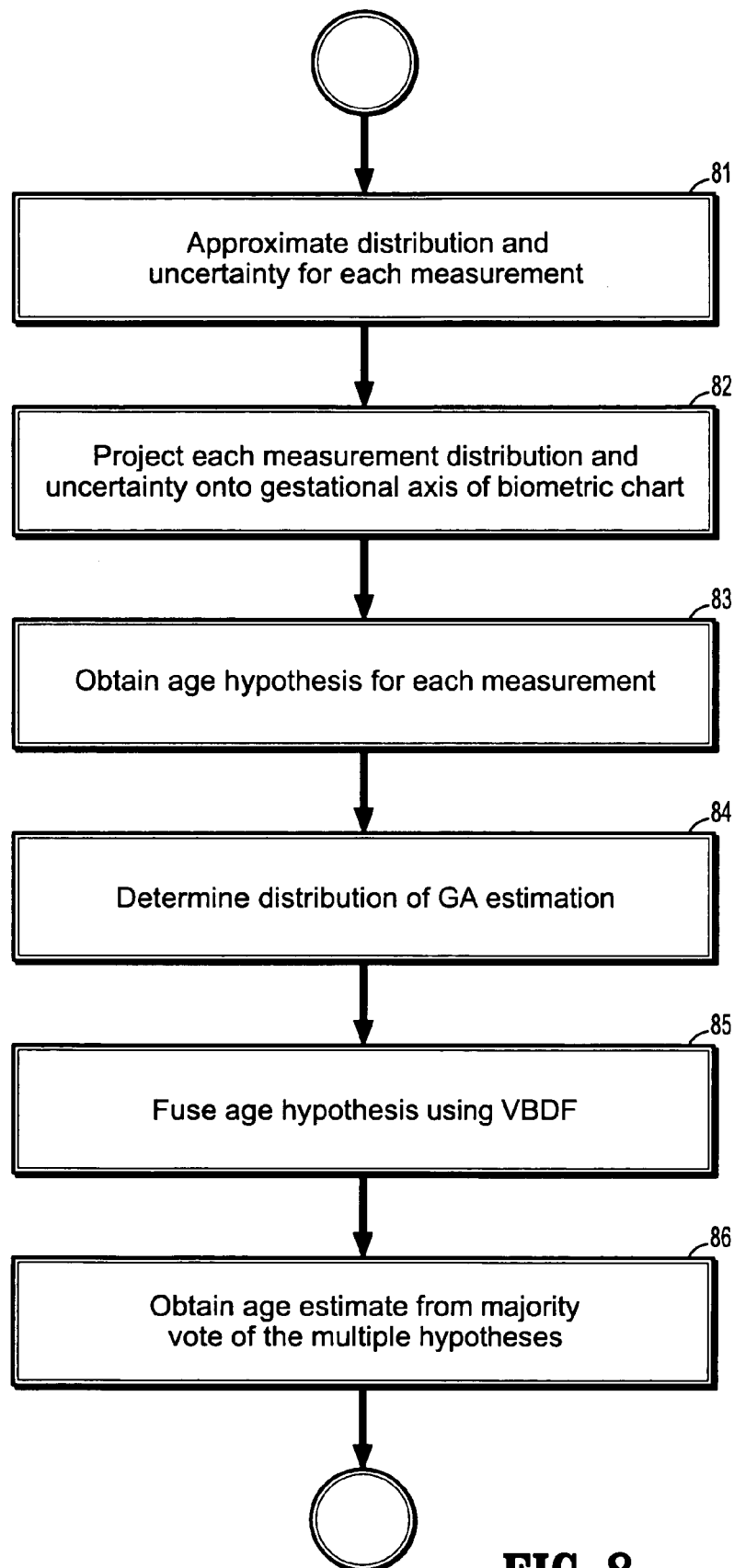
FIG. 8 is a flow chart of a method for fetal gestational age estimation according to an embodiment of the invention.

FIG. 8 is a flow chart of a method for fetal gestational age estimation according to an embodiment of the invention. Referring to the figure, a probability distribution function and measurement uncertainty is approximated at step 81 for each measurement. Such a method should use at least two fetal biometric parameters, including the uncertainty of their measurements. Exemplary measurement combinations include head and abdomen, head and femur, and femur and abdomen. The accuracy of the measurement improves as the number of measurements and the variability of the measurements increases. The uncertainty of an individual measurement can be represented as a confidence interval, a normal distribution with a known variance or, generally, an arbitrary parametric or nonparametric distribution. The distribution of each individual measurement is projected at step 82 onto the GA chart, and can then be projected onto the GA axis in order to compute at step 83 the distribution of the GA estimation of the particular measurement. Due to the nonlinearities of the charts and skewness (the lack of symmetry) of individual measurement distributions, numerical sampling techniques are used to estimate the distribution of the GA. Individual GA estimators may be noisy and it is desired that the GA estimation be robust to the presence of outliers. A hypothesis of the GA is obtained from the GA distribution at step 84. At step 85, multiple distributions are robustly fused using the Variable Bandwidth Density-based Fusion (VBDF) described below, using the algorithm reminiscent of majority voting. At step 86, a GA estimate is obtained from a majority vote of the various individual hypotheses. As the measurement uncertainties are propagated through all stages of GA estimation process, the final GA estimator includes a variance that is the robust summary of all individual measurement uncertainties.

Figure 3:
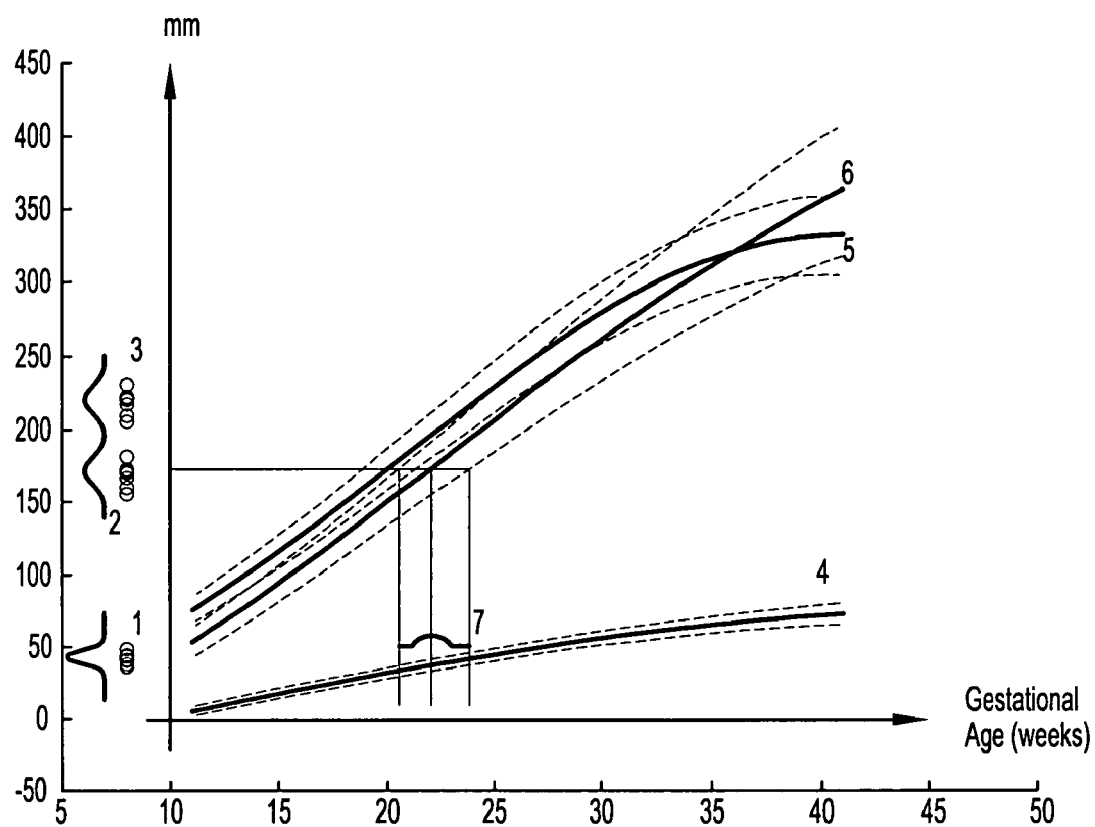
FIG. 3 illustrates the fusion of multiple fetal measurements to obtain a robust estimation of gestational age, according to an embodiment of the invention.

An illustration of the fusion of multiple fetal measurements according to an embodiment of the invention to obtain a robust estimation of gestational age is presented in FIG. 3. The x-axis represents the gestational age in weeks. On the y-axis are illustrated three common fetal measurements in millimeters: the femur 1, the abdominal circumference 2, and the head circumference 3, together with their measurement uncertainties, depicted as Gaussian distributions. Each distribution is approximated with a number of samples obtained using Monte Carlo sampling. The collection of samples is back projected (illustrated for the case of abdominal circumference) onto the gestational age axis using standardized biometric charts, shown as the solid lines 4, 5, 6, together with confidence intervals shown with dotted lines. Due to the statistical nature of the charts, each individual measurement yields multiple hypotheses for the gestational age according to the distribution 7 that is computed assuming the chart uncertainties are normally distributed. The collection of gestational age hypotheses 7 is computed for each particle and for each measurement (head, abdomen, and femur). The variable bandwidth density-based fusion (VBDF) is then used to robustly compute the majority vote of the multiple hypotheses and produce the final estimation of the gestational age.

Adaptive density estimation with a variable bandwidth kernel can adapt kernel scaling and orientation to local data statistics. Let $x_i$, $i=1, \ldots n$, be n data points in a d-dimensional space $R^d$. By selecting a different bandwidth matrix $H_i = H(x_i)$ for each $x_i$, one can define a sample point density estimator $$\hat{f}_v(x) = \frac{1}{n(2\pi)^{d/2}} \sum_{i=1}^{n} \frac{1}{|H_i|^{1/2}} \exp\left(-\frac{1}{2} D^2(x, x_i, H_i)\right),$$

where $$D^2(x, x_i, H_i) \equiv (x - x_i)^T H_i^{-1} (x - x_i)$$

is the Mahalanobis distance from x to $x_i$. The variable-bandwidth mean shift vector at location x is given by $$m_v(X) \equiv H_h(x) \sum_{i=1}^{n} \omega_i(x) H_i^{-1}(x_i - x),$$

where $H_h$ is the data-weighted harmonic mean of the bandwidth matrices computed at x $$H_h(x) \left( \sum_{i=1}^{n} w(x) H_i^{-1} \right)^{-1},$$

and $$\omega_i(x) = \frac{\frac{1}{|H_i|^{1/2}} \exp\left(-\frac{1}{2} D^2(x, x_i, H_i)\right)}{\sum_{i=1}^{n} \frac{1}{|H_i|^{1/2}} \exp\left(-\frac{1}{2} D^2(x, x_i, H_i)\right)}$$

are weights satisfying $$\sum_{i=1}^{n} \omega_i(x) = 1.$$

The interative computation of the mean shift vector always moves the point x to a location where the density $\hat{f}_v(x)$ is greater than or equal to the density at the previous location. As a result, an iterative hill-climbing procedure can be defined which converges to a stationary point (i.e. zero gradient) of the underlying density.

The VBDF estimator is defined as the location of the most significant sample mode of the data. Assume that the data points $x_i$, $i=1, \ldots n$, are each associated with a covariance matrix $C_i$ that quantifies uncertainty. The location of the most significant mode is obtained in a multi-scale manner, by tracking the mode of the density function cores scales. A first mode detection is performed using large bandwidth matrices of the form $H_i = C_i + \alpha^2 I$, where the parameter $\alpha$ is large with respect to the spread of the points $x_i$. The mode detection technique is based on mean shift and involves the iterative computation and translation of x by $m_v(x)$ until convergence. At the largest scale, the mode location does not depend on the initialization (up to some numerical approximation error) since for a large $\alpha$ the density surface is unimodal.

In the next stages, the detached mode is tracked across scales by successively reducing the parameter $\alpha$ and performing mode detection again. At each scale the mode detection technique is initialized with the convergence location from the previous scale. For the last mode detection step, the bandwidth matrix associated with each data point is equal to the point covariance matrix, i.e. $H_i = C_i$, $i=1, \ldots n$. The location of the most significant mode can be represented by $\hat{x}_m$. Since the gradient at $\hat{x}_m$ is zero, $m_v(\hat{x}_m) = 0$, which means $$\hat{x}_m = H_h(\hat{x}_m) \sum_{i=1}^{n} \omega_i(\hat{x}_m) H_i^{-1} x_i,$$

$$H_h(\hat{x}_m) = \left( \sum_{i=1}^{n} \omega_i(\hat{x}_m) H_i^{-1} \right)^{-1}.$$

For a given image location, one can extract an initial motion estimate from a very small N % N neighborhood using Biased Least Squares (BLS), $$\hat{x} = (A^T A + \beta I)^{-} A^T b,$$

where A is the $N^2$ % 2 matrix of spatial image gradients, and b is the $N^2$-dimensional vector of temporal images. The BLS solution has a covariance matrix C that is proportional to the variance $\sigma^2$ of the image noise. The BLS method avoids instability issues in the regular least squares solution by allowing a small amount of bias.

Motion flow information can be combined in a local image neighborhood of dimension n=M % M using the VBDF estimator. Denoting the initial flow estimates produced through BLS by $(\hat{x}_i, C_i) i=1, \ldots n$, their fusion results in $$\hat{x}_m = C(\hat{x}_m) \sum_{i=1}^{n} \omega_i(\hat{x}_m) C_i^{-1} \hat{x}_i,$$

and $\hat{x}_m$ is determined through mode tracking across scales, as discussed above.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 9:
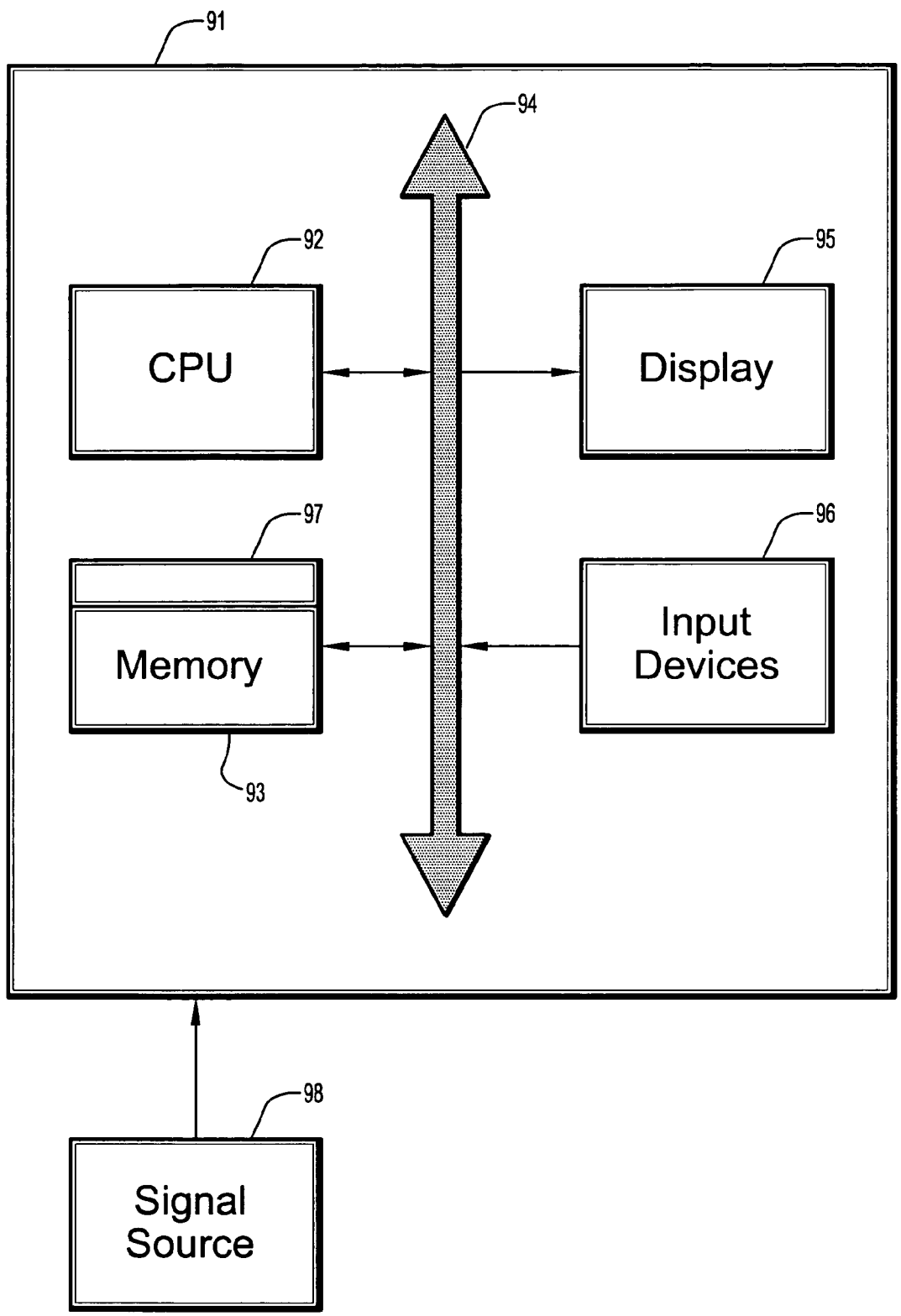
FIG. 9 is a block diagram of an exemplary computer system for implementing a fetal biometric measurement and fusion method according to an embodiment of the invention.

FIG. 9 is a block diagram of an exemplary computer system for implementing a method for automatically detecting, segmenting, and measuring fetal anatomical structures from ultrasound images in real-time, according to an embodiment of the invention. Referring now to FIG. 9, a computer system 91 for implementing the present invention can comprise, inter alia, a central processing unit (CPU) 92, a memory 93 and an input/output (I/O) interface 94. The computer system 91 is generally coupled through the I/O interface 94 to a display 95 and various input devices 96 such as a mouse and a keyboard. The support circuits can include circuits such as cache, power supplies, clock circuits, and a communication bus. The memory 93 can include random access memory (RAM), read only memory (ROM), disk drive, tape drive, etc., or a combinations thereof. The present invention can be implemented as a routine 97 that is stored in memory 93 and executed by the CPU 92 to process the signal from the signal source 98. As such, the computer system 91 is a general purpose computer system that becomes a specific purpose computer system when executing the routine 97 of the present invention.

The computer system 91 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for segmenting and measuring anatomical structures in fetal ultrasound images comprising the steps of:
providing a digitized 3-dimensional ultrasound image of a fetus comprising a plurality of intensities corresponding to a domain of points on a 3-dimensional grid;
providing a plurality of classifiers trained to detect anatomical structures in said image of said fetus;
segmenting and measuring an anatomical structure using said image classifiers by applying elliptical contour classifiers to said fetal ultrasound image, wherein a plurality of 2-dimensional contours characterizing said anatomical structure are detected; and
combining said anatomical structure measurement with measurement of another anatomical structure to estimate gestational age of said fetus by approximating a distribution and uncertainty for each measurement, projecting each measurement distribution and uncertainty onto a gestational age axis of a gestational biometric chart to obtain a gestational age hypothesis for each measurement, estimating the distribution of the gestational age hypotheses, and fusing said age hypotheses using a variable bandwidth density-based fusion wherein a majority vote of said multiple hypotheses estimates said gestational age.

2. The method of claim 1, wherein said classifiers are trained to detect anatomical structures by providing a set of ellipses to represent contours of said anatomical structures, providing a database of pairs of contours and intensity sets that are represented by said contour, using a boosting technique with said database for training said classifiers to correctly detect contour/intensity-set pairs, but reject most non-contour/intensity-set pairs, and incorporating some non-contour/intensity-set pairs into said classifier, wherein said trained classifier outputs an image model that maps a set of image intensities to a likelihood of a presence of an anatomical structure.

3. The method of claim 2, wherein said classifiers explicitly incorporate translation, rotation, and scaling of said intensity-sets.

4. The method of claim 2, wherein said contour/intensity pairs in said database were selected by one or more experts in obstetrics.

5. The method of claim 1, wherein segmenting and measuring further comprise sweeping said 3-dimensional ultrasound fetal image wherein a plurality of planes are obtained by uniformly sampling the azimuthal and elevation angles; and
for each plane of said plurality of planes, applying said contour classifiers to a plurality of locations, scales, orientations, and aspect ratios.

6. The method of claim 5, further comprising propagating said 2-dimensional contours to form a 3-dimensional shape of said anatomical structure.

7. The method of claim 2, wherein training said contour classifier comprises registering said contours to ellipses by learning global transformations, wherein global transformations include translation, scale, rotation, and aspect ratio, and applying an inverse global transformation.

8. The method of claim 7, wherein said ellipses include contours that deviate slightly from a perfect ellipse.

9. The method of claim 1, wherein said anatomical measurements include two or more measurements selected from the group including of fetal crown-rump length, head circumference, bi-parietal diameter, abdominal diameter, occipital-frontal diameter, and femur length.

10. A non-transitory program storage device readable by a computer, tangibly embodying a program of instructions executable by the computer to perform the method steps for segmenting and measuring anatomical structures in fetal ultrasound images, said method comprising the steps of:
providing a digitized 3-dimensional ultrasound image of a fetus comprising a plurality of intensities corresponding to a domain of points on a 3-dimensional grid;
providing a plurality of classifiers trained to detect anatomical structures in said image of said fetus;
segmenting and measuring an anatomical structure using said image classifiers by applying elliptical contour classifiers to said fetal ultrasound image, wherein a plurality of 2-dimensional contours characterizing said anatomical structure are detected; and
combining said anatomical structure measurement with measurement of another anatomical structure to estimate gestational age of said fetus by approximating a distribution and uncertainty for each measurement, projecting each measurement distribution and uncertainty onto a gestational age axis of a gestational biometric chart to obtain a gestational age hypothesis for each measurement, estimating the distribution of the gestational age hypotheses, and fusing said age hypotheses using a variable bandwidth density-based fusion wherein a majority vote of said multiple hypotheses estimates said gestational age.

11. The computer readable program storage device of claim 10, wherein said classifiers are trained to detect anatomical structures by providing a set of ellipses to represent contours of said anatomical structures, providing a database of pairs of contours and intensity sets that are represented by said contour, using a boosting technique with said database for training said classifiers to correctly detect contour/intensity-set pairs, but reject most non-contour/intensity-set pairs, and incorporating some non-contour/intensity-set pairs into said classifier, wherein said trained classifier outputs an image model that maps a set of image intensities to a likelihood of a presence of an anatomical structure.

12. The computer readable program storage device of claim 11, wherein training said contour classifier comprises registering said contours to ellipses by learning global transformations, wherein global transformations include translation, scale, rotation, and aspect ratio, and applying an inverse global transformation.

13. The computer readable program storage device of claim 12, wherein said ellipses include contours that deviate slightly from a perfect ellipse.

14. The computer readable program storage device of claim 11, wherein said classifiers explicitly incorporate translation, rotation, and scaling of said intensity-sets.

15. The computer readable program storage device of claim 11, wherein said contour/intensity pairs in said database were selected by one or more experts in obstetrics.

16. The computer readable program storage device of claim 10, wherein segmenting and measuring further comprise sweeping said 3-dimensional ultrasound fetal image wherein a plurality of planes are obtained by uniformly sampling the azimuthal and elevation angles; and for each plane of said plurality of planes, applying said contour classifiers to a plurality of locations, scales, orientations, and aspect ratios.

17. The computer readable program storage device of claim 16, the method further comprising propagating said 2-dimensional contours to form a 3-dimensional shape of said anatomical structure.

18. The computer readable program storage device of claim 10, wherein said anatomical measurements include two or more measurements selected from the group including of fetal crown-rump length, head circumference, bi-parietal diameter, abdominal diameter, occipital-frontal diameter, and femur length.

* * * * *